United States Patent
Samatar et al.

(10) Patent No.: US 11,278,532 B2
(45) Date of Patent: Mar. 22, 2022

(54) ESTROGEN RECEPTOR MODULATORS FOR TREATING MUTANTS

(71) Applicant: RECURIUM IP HOLDINGS, LLC, San Diego, CA (US)

(72) Inventors: Ahmed Abdi Samatar, West Windsor, NJ (US); Jiali Li, San Diego, CA (US); Jianhui Ma, San Diego, CA (US); Sayee Gajanan Hegde, San Diego, CA (US); Peter Qinhua Huang, San Diego, CA (US); Kevin Duane Bunker, Escondido, CA (US); Fernando Donate, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/985,004

(22) Filed: Aug. 4, 2020

(65) Prior Publication Data
US 2021/0038573 A1 Feb. 11, 2021

Related U.S. Application Data

(60) Provisional application No. 63/009,746, filed on Apr. 14, 2020, provisional application No. 62/883,395, filed on Aug. 6, 2019.

(51) Int. Cl.
*A61K 31/437* (2006.01)
*A61P 35/00* (2006.01)

(52) U.S. Cl.
CPC ............ *A61K 31/437* (2013.01); *A61P 35/00* (2018.01)

(58) Field of Classification Search
CPC .................................................. A61K 31/437
See application file for complete search history.

(56) References Cited

U.S. PATENT DOCUMENTS

| | | |
|---|---|---|
| 2014/0018433 A1 | 1/2014 | Dalton et al. |
| 2014/0235660 A1 | 8/2014 | Burks et al. |
| 2015/0315198 A1 | 11/2015 | Li et al. |
| 2017/0368003 A1 | 12/2017 | Narayanan et al. |
| 2017/0368036 A1* | 12/2017 | Hattersley ............ A61K 31/436 |
| 2018/0170943 A1 | 6/2018 | Yu et al. |
| 2018/0273487 A1 | 9/2018 | Narayanan et al. |

(Continued)

FOREIGN PATENT DOCUMENTS

| | | |
|---|---|---|
| CN | 102432608 | 5/2012 |
| CN | 104693211 A | 6/2015 |

(Continued)

OTHER PUBLICATIONS

Angus et al., "*ESR1* mutations: Moving towards guiding treatment decision-making in metastatic breast cancer patients" Cancer Treatment Reviews (2017) 52:33-40.

(Continued)

*Primary Examiner* — Benjamin J Packard
(74) *Attorney, Agent, or Firm* — Knobbe Martens Olson & Bear LLP

(57) ABSTRACT

Uses and methods that include an effective amount of Compound (A), or a pharmaceutically acceptable salt thereof, are described herein for treating breast cancer in a subject in need thereof, wherein the breast cancer has at least one point mutation within the Estrogen Receptor 1 (ESR1) that encodes Estrogen receptor alpha (ERα).

22 Claims, 7 Drawing Sheets

(56) References Cited

U.S. PATENT DOCUMENTS

| | | |
|---|---|---|
| 2018/0291019 A1 | 10/2018 | Guan et al. |
| 2020/0261428 A1 | 8/2020 | Huang et al. |
| 2020/0261429 A1 | 8/2020 | Huang et al. |
| 2020/0261430 A1 | 8/2020 | Huang et al. |

FOREIGN PATENT DOCUMENTS

| | | |
|---|---|---|
| CN | 105229004 A | 6/2016 |
| CN | 107428758 A | 12/2017 |
| CN | 108329311 A | 7/2018 |
| CN | 109362222 A | 2/2019 |
| EA | 16160 | 2/2012 |
| EP | 3378861 | 9/2018 |
| JP | 2001-294575 A | 10/2001 |
| JP | 2015-503526 A | 2/2016 |
| MX | 2017007489 | 6/2017 |
| MX | 2018009496 | 8/2018 |
| RU | 2472782 | 1/2013 |
| TW | 201700461 A | 1/2017 |
| WO | WO 95/24200 | 9/1995 |
| WO | WO 9732860 | 9/1997 |
| WO | WO 2003/033496 | 4/2003 |
| WO | WO 2006/015035 | 2/2006 |
| WO | WO 2007/002051 | 1/2007 |
| WO | WO 2008/002490 | 1/2008 |
| WO | WO 2008/127714 | 10/2008 |
| WO | WO 2008/127715 | 10/2008 |
| WO | WO 2010/083136 | 7/2010 |
| WO | WO 2010/107485 | 9/2010 |
| WO | WO 2011/088025 | 7/2011 |
| WO | WO 2011/103487 | 8/2011 |
| WO | WO 2011/156518 | 12/2011 |
| WO | WO 2013/090829 | 6/2013 |
| WO | WO 2013/090836 | 6/2013 |
| WO | WO 2013/142266 | 9/2013 |
| WO | WO 2014/151899 | 9/2014 |
| WO | WO 2014/191726 | 12/2014 |
| WO | WO 2015/082990 | 6/2015 |
| WO | WO 2015/171527 | 11/2015 |
| WO | WO 2015/173329 | 11/2015 |
| WO | WO 2015/197861 | 12/2015 |
| WO | WO 2016/054971 | 4/2016 |
| WO | WO 2016/172358 | 10/2016 |
| WO | WO 2017/080338 | 5/2017 |
| WO | WO 2017/136688 | 8/2017 |
| WO | WO 2017/172957 | 10/2017 |
| WO | WO 2017214634 | 12/2017 |
| WO | WO 2018/001232 | 1/2018 |
| WO | WO 2018/065501 | 4/2018 |
| WO | WO 2018/130124 | 7/2018 |

OTHER PUBLICATIONS

Fanning et al., "Estrogen receptor alpha somatic mutations Y537S and D538G confer breast cancer endocrine resistance by stabilizing the activating function-2 binding conformation" eLIFE (2016) 5:e12792.

Jeselsohn et al., "*ESR1* mutations—a mechanism for acquired endocrine resistance in breast cancer" Nature Reviews. Nat. Rev. Clin. Oncol. (2015) 12(10):573-583.

Spoerke et al., "Heterogeneity and clinical significance of *ESR1* mutations in ER-positive metastatic breast cancer patients receiving fulvestrant" Nature Communications (2016) 7:e11579.

Toy et al., "*ESR1* ligand-binding domain mutations in hormone-resistant breast cancer" Nature Genetics (2013) 45(12):1439-1445.

Toy et al., "Activating *ESR1* Mutations Differentially Impact the Efficacy of ER Antagonists" Cancer Discovery (2017) 7(3):277-287.

Weir et al., "AZD9496: An Oral Estrogen Receptor Inhibitor That Blocks the Grown ER-Positive and ESR1-Mutant BreastTumors in Preclinical Models" Cancer Research (2016) 76(11):3307-3318.

International Search Report and Written Opinion dated Sep. 2, 2020 for PCT Application No. PCT/US2020/044884, filed Aug. 4, 2020.

Bragg, et al., "The synthesis of tritium, carbon-14 and stable isotope labelled selective estrogen receptor degraders", Journal of Labelled Compounds and Radiopharmaceuticals (2016) 59(11):454-461.

De Savi, et al., "Optimization of a Novel Binding Motif to (E) 3-(3,5-Difluoro-4-((1R,3R)2-(2-fluoro-2-methylpropyl)-3-methyl-2,3,4,9-tetrahydro-1Hpyrido[3,4b]indol-1-yl)phenyl)acrylie Acid (AZD9496), a Potent and Orally Bioavailable Selective Estrogen Receptor Downregulator and Antagonist", J. Med. Chern. (2015) 58:8128-8140.

De Savi, Chris, "Discovery of AZD9496: an oral, selective estrogen receptor down-regulator (SERD)" Gordon Research Conference (Aug. 2-7, 2015).

Filosa, R. et al., "Design, synthesis and biological evaluation of novel bicyclo[1.1.1]pentane-based ω-acidic amino acids as glutamate receptors ligands". Bioorganic & Medicinal Chemistry (2009) 17 (1):242-250.

Garner, et al., "RAD1901: a novel, orally bioavailable selective estrogen receptor degrader that demonstrates antitumor activity in breast cancer xenograft models" Anti-Cancer Drugs (2015) 26(9):948-956.

Gobe, et al., "Self-Relay Gold(I)-Catalyzed Pictet-Spengler/ Cyclization Cascade Reaction for the Rapid Elaboration of Pentacyclic Indole Derivatives", Chem. Eur. J. (2015), 21(49):17587-17590.

Lai, et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", J. Med. Chem. (2015) 58:4888-4904.

McDonnell, et al., "Oral Selective Estrogen Receptor Downregulators (SERDs), a Breakthrough Endocrine Therapy for Breast Cancer", J. Med. Chem. (2015) 58(12):4883-4887.

Samatar, et al. "Discovery of ZN-c5 a Novel Potent and Oral Selective Estrogen Receptor Degrader", Poster #4373, AACR Virtual Annual Meeting (Jun. 22, 2020).

Walji, et al., "Discovery of MK-8970: An Acetal Carbonate Prodrug of Raltegravir with Enhanced Colonic Absorption," ChemMedChem (2015) 10:245-252.

* cited by examiner

Figure 1

| Name | Structure |
|---|---|
| (E)-3-[3,5-Difluoro-4-[(1R,3R)-2-(2-fluoro-2-methylpropyl)-3-methyl-1,3,4,9-tetrahydropyrido[3,4-b]indol-1-yl]phenyl]prop-2-enoic acid (AZD9496) | 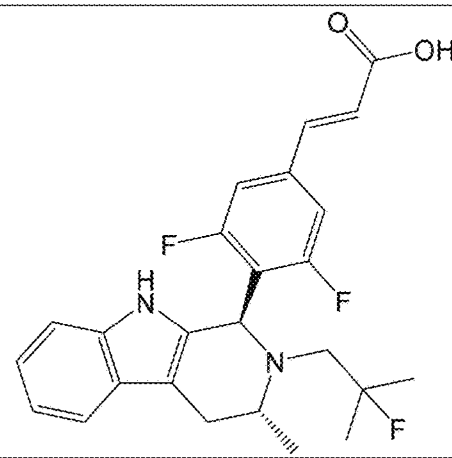 |
| (R)-6-(2-(ethyl(4-(2-(ethylamino)ethyl)benzyl)amino)-4-methoxyphenyl)-5,6,7,8-tetrahydronaphthalen-2-ol (elacestrant, RAD1901) | 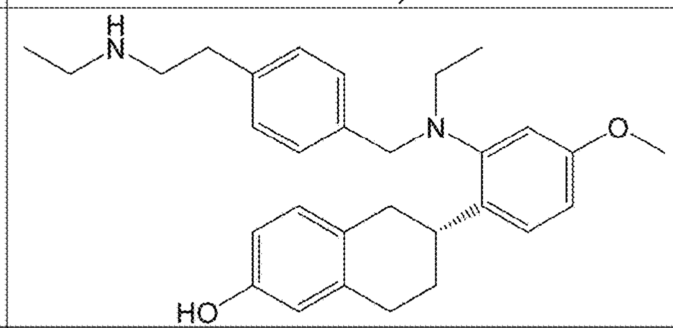 |
| (E)-3-(4-((E)-2-(2-chloro-4-fluorophenyl)-1-(1H-indazol-5-yl)but-1-en-1-yl)phenyl)acrylic acid (Brilanestrant, ARN-810, GDC-0810) | 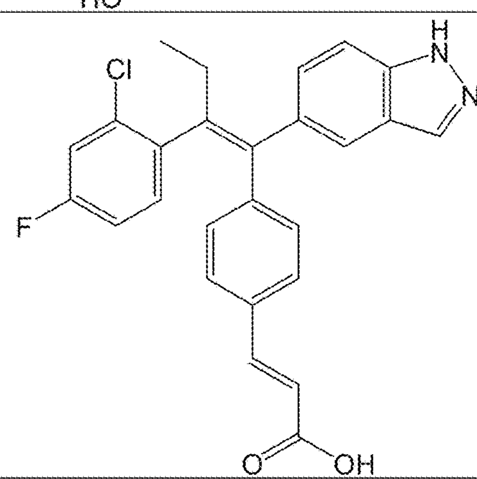 |

Figure 1 (cont.)

| Name | Structure |
|---|---|
| (E)-3-(4-((2-(2-(1,1-difluoroethyl)-4-fluorophenyl)-6-hydroxybenzo[b]thiophen-3-yl)oxy)phenyl)acrylic acid | 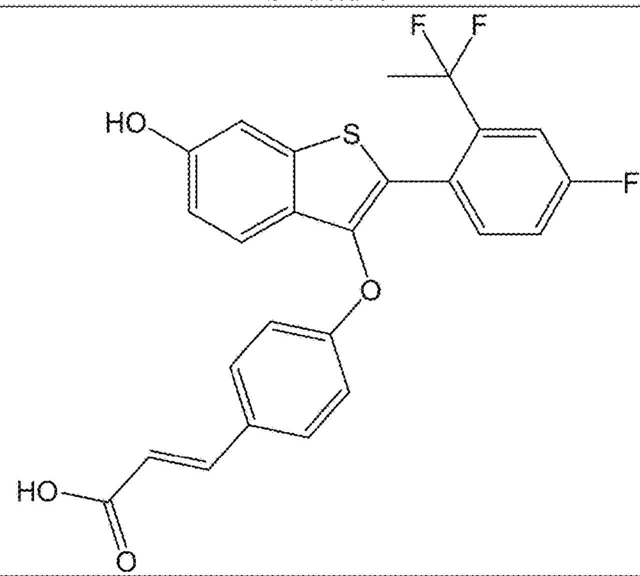 |
| (E)-3-(4-((2-(4-fluoro-2,6-dimethylbenzoyl)-6-hydroxybenzo[b]thiophen-3-yl)oxy)phenyl)acrylic acid | 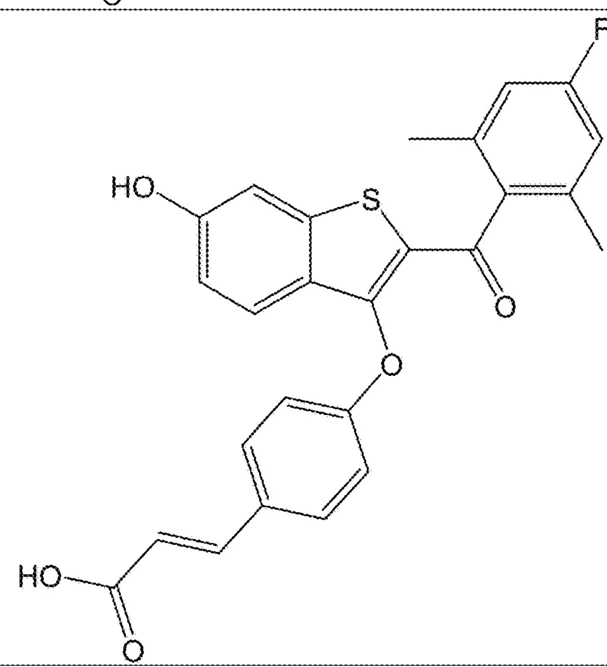 |

Figure 1 (cont.)

| Name | Structure |
|---|---|
| (S)-8-(2,4-dichlorophenyl)-9-(4-((1-(3-fluoropropyl)pyrrolidin-3-yl)oxy)phenyl)-6,7-dihydro-5H-benzo[7]annulene-3-carboxylic acid | 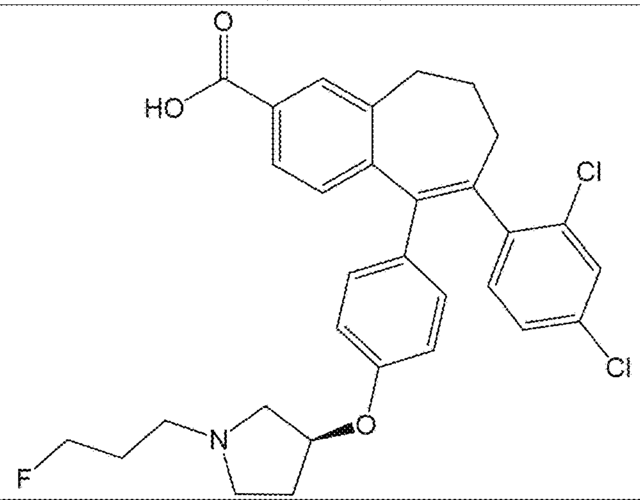 |
| 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol | 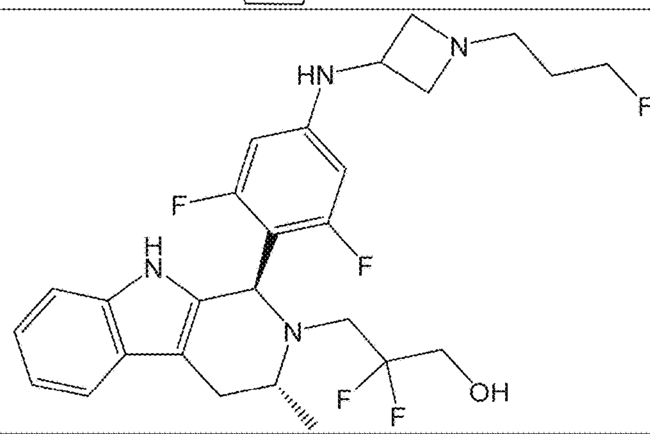 |

ESTROGEN RECEPTOR MODULATORS FOR TREATING MUTANTS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 62/883,395, filed Aug. 6, 2019, and 63/009,746, filed Apr. 14, 2020.

FIELD

The present application relates to methods for treating breast cancer with a compound that is estrogen receptor alpha modulator, wherein the breast cancer has at least one point mutation within Estrogen Receptor 1 (ESR1).

DESCRIPTION

The estrogen receptor (ER) belongs to a family of nuclear hormone receptors and acts as a ligand-dependent transcription factor. Upon the binding of estrogen, a conformational change occurs which allows for the binding of co-activator(s). The binding of estrogen regulates the transcription of multiple genes involved in various physiological and cancer-related processes.

A number of breast cancer drug therapies have been developed that target ERs. Within ESR1, several amino acid mutations have been identified. Mutations in ESR1 have been proposed as playing a role in resistance.

SUMMARY

Some embodiments disclosed herein are directed to the use of an effective amount of Compound (A), or a pharmaceutically acceptable salt thereof, in the manufacture for a medicament for treating breast cancer in a subject in need thereof, wherein the breast cancer has at least one point mutation within the Estrogen Receptor 1 (ESR1) that encodes Estrogen receptor alpha (ERα).

Other embodiments disclosed herein are directed to the use of an effective amount of Compound (A), or a pharmaceutically acceptable salt thereof, for treating breast cancer in a subject in need thereof, wherein the breast cancer has at least one point mutation within the Estrogen Receptor 1 (ESR1) that encodes Estrogen receptor alpha (ERα).

Still other embodiments disclosed herein are directed to a method of treating breast cancer in a subject in need thereof with an effective amount of Compound (A), or a pharmaceutically acceptable salt thereof, wherein the breast cancer has at least one point mutation within the Estrogen Receptor 1 (ESR1) that encodes Estrogen receptor alpha (ERα).

BRIEF DESCRIPTION OF THE DRAWINGS

FIG. 1 provides the name and structure of certain cancer therapy compounds.

DETAILED DESCRIPTION

Figure 2:
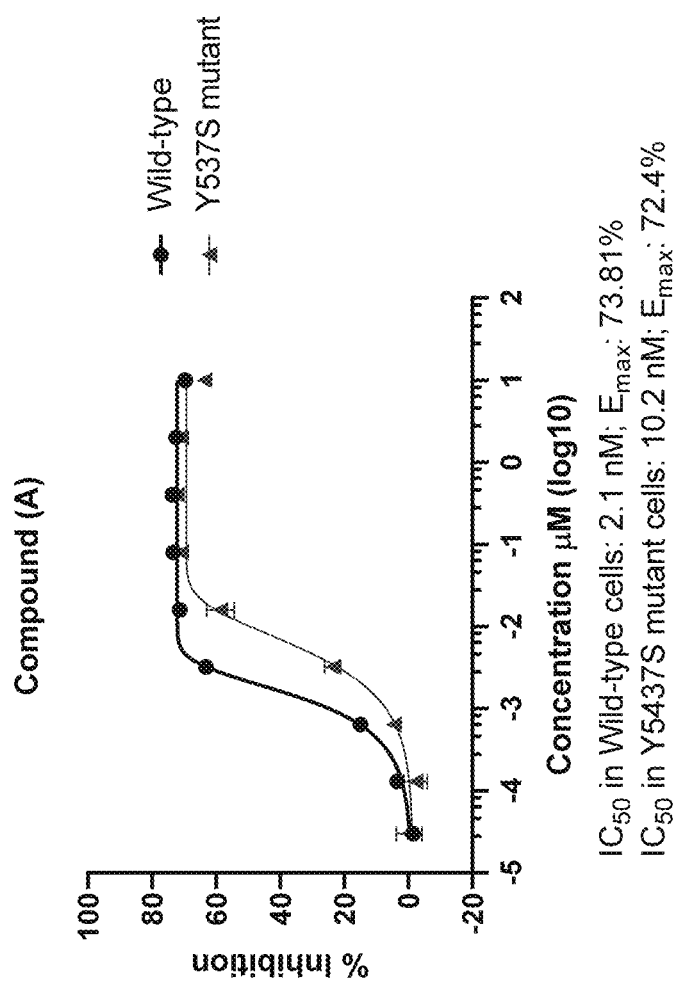
FIG. 2 shows the results of a study with Compound (A) in a wild-type breast cancer cell line and a breast cancer cell line that has a Y537S mutation.

There are several therapies for inhibiting estrogen receptors, including selective ER modulators (SERM), selective ER degraders (SERD) and aromatase inhibitors. One issue that can arise from the aforementioned cancer therapies is the development of resistance to the cancer therapy. Acquired resistance to cancer therapy, such as endocrine therapy, has been noted in nearly one-third of women treated with tamoxifen and other endocrine therapies. See Alluri et al., "Estrogen receptor mutations and their role in breast cancer progression" Breast Cancer Research (2014) 16:494.

Researchers have suspected mutations in the estrogen receptor as one of the reasons for acquired resistance to cancer therapy, such as endocrine therapy. Thus, there is a need for compounds that can treat breast cancer wherein the cancer has one or more mutations within ESR1. Several ESR1 mutants in the ligand-binding domain have been detected and studied. Further, it has been noted that the prevalence of mutations is low in subjects that have been diagnosed with breast cancer, but have not yet initiated a cancer therapy.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine and salts with amino acids such as arginine and lysine. For Compound (A), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

As used herein, the terms "treat," "treating," "treatment," "therapeutic," and "therapy" do not necessarily mean total cure or abolition of the estrogen receptor dependent and/or estrogen receptor mediated disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the estrogen receptor dependent and/or estrogen receptor mediated disease or condition, or prolong the survival of the subject being treated This response may occur in a tissue, system, animal or human and includes alleviation of the signs or symptoms of the estrogen receptor dependent and/or estrogen receptor mediated disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compound A

Compound A has the structure:

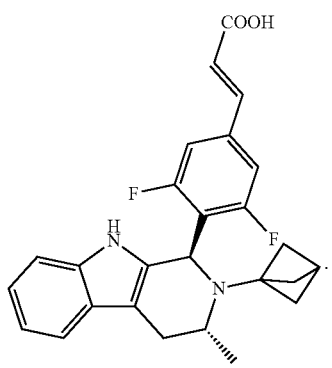 [SMILES: C[C@@H]1Cc2c([nH]c3ccccc23)[C@@H](c2c(F)cc(/C=C/C(=O)O)cc2F)N1C12CC(C1)C2]

Compound A ((E)-3-(4-((1R,3R)-2-(Bicyclo[1.1.1]pentan-1-yl)-3-methyl-2,3,4,9-tetrahydro-1H-pyrido[3,4-b]indol-1-yl)-3,5-difluorophenyl)acrylic acid), along with its pharmaceutically acceptable salts, can be prepared following the procedures provided in WO 2017/172957. As provided in WO 2017/172957, Compound A is active against Estrogen receptor alpha (ERα).

In some embodiments, Compound A, or a pharmaceutically acceptable salt thereof, can be administered to the subject via a pharmaceutical composition, wherein the pharmaceutical composition includes an effective amount of Compound (A), or a pharmaceutically acceptable salt thereof, and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as anti-oxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Uses and Methods of Treatment

Some embodiment disclosed herein are directed to the use of an effective amount of a compound in the manufacture for a medicament for treating breast cancer in a subject in need thereof, wherein the breast cancer has at least one point mutation within the Estrogen Receptor 1 (ESR1) that encodes Estrogen receptor alpha (ERα). Other embodiments disclosed herein are directed to a method of treating breast cancer in a subject in need thereof with an effective amount of a compound of Compound (A), or a pharmaceutically acceptable salt thereof, wherein the breast cancer has at least one point mutation within the Estrogen Receptor 1 (ESR1) that encodes Estrogen receptor alpha (ERα).

In some embodiments, the mutation can be in the ligand binding domain (LBD) of ESR1. In some embodiments, one or more mutations can be at an amino acid selected from: A593, S576, G557, R555, L549, A546, E542, L540, D538, Y537, L536, P535, V534, V533, N532, K531, C530, H524, E523, M522, R503, L497, K481, V478, R477, E471, S463, F461, S432, G420, V418, D411, L466, S463, L453, G442, M437, M421, M396, V392, M388, E380, G344, S338, L370, S329, K303, A283, S282, E279, G274, K252, R233, P222, G160, N156, P147, G145, F97, N69, A65, A58 and S47. In some embodiments, one or more mutations can be at an amino acid selected from: D538, Y537, L536, P535, V534, S463, V392 and E380. In some embodiments, one or more mutations can be at an amino acid selected from: D538 and Y537.

In some embodiments, one or more mutations can be selected from: K303R, D538G, Y537S, E380Q, Y537C, Y537N, A283V, A546D, A546T, A58T, A593D, A65V, C530L, D411H, E279V, E471D, E471V, E523Q, E542G, F461V, F97L, G145D, G160D, G274R, G344D, G420D, G442R, G557R, H524L, K252N, K481N, K531E, L370F, L453F, L466Q, L497R, L536H, L536P, L536Q, L536R, L540Q, L549P, M388L, M396V, M421V, M437I, M522I, N156T, N532K, N69K, P147Q, P222S, P535H, R233G, R477Q, R503W, R555H, S282C, S329Y, S338G, S432L, S463P, S47T, S576L, V392I, V418E, V478L, V533M, V534E, Y537D and Y537H.

The number of mutations in the ligand binding domain (LBD) can vary. For example, one mutation can be present in the ligand binding domain (LBD). As another example, two, three or four or more mutations can be present in the ligand binding domain (LBD). In some embodiments, the mutation can be Y537S. In some embodiments, the mutation can be L536P.

As provided herein, several studies have shown that a potential cause of resistance in ER-positive breast cancer is due to acquired mutations in ESR1 due to endocrine therapy. In some embodiments, the subject had been previously treated with one or more selective ER modulators. For example, subject had been treated previously with one or more selected ER modulators selected from tamoxifen, raloxifene, ospemifene, bazedoxifene, toremifene and lasofoxifene. In some embodiments, the subject had been treated previously with one or more selective ER degraders, such as fulvestrant, elacestrant, (E)-3-[3,5-Difluoro-4-[(1R,3R)-2-(2-fluoro-2-methylpropyl)-3-methyl-1,3,4,9-tetrahydro-pyrido[3,4-b]indol-1-yl]phenyl]prop-2-enoic acid (AZD0496)), (R)-6-(2-(ethyl(4-(2-(ethylamino)ethyl)benzyl)amino)-4-methoxyphenyl)-5,6,7,8-tetrahydronaphthalen-2-ol (elacestrant, RAD1901), (E)-3-(4-((E)-2-(2-chloro-4-fluorophenyl)-1-(1H-indazol-5-yl)but-1-en-1-yl)phenyl) acrylic acid (Brilanestrant, ARN-810, GDC-0810), (E)-3-(4-((2-(2-(1,1-difluoroethyl)-4-fluorophenyl)-6-hydroxybenzo[b]thiophen-3-yl)oxy)phenyl)acrylic acid, (E)-3-(4-((2-(4-fluoro-2,6-dimethylbenzoyl)-6-hydroxy-benzo[b]thiophen-3-yl)oxy)phenyl)acrylic acid, (S)-8-(2,4-dichlorophenyl)-9-(4-((1-(3-fluoropropyl)pyrrolidin-3-yl) oxy)phenyl)-6,7-dihydro-5H-benzo[7]annulene-3-carboxylic acid and/or 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol. In some embodiments, the subject had been treated previously with one or more aromatase inhibitors. The aromatase inhibitors can be a steroidal aromatase inhibitor or a non-steroidal aromatase inhibitor. For example, the one or more aromatase inhibitors can be selected from (exemestane (steroidal aromatase inhibitor), testolactone (steroidal aromatase inhibitor); anastazole (non-steroidal aromatase inhibitor) and letrazole (non-steroidal aromatase inhibitor).

In some embodiments, the subject can be a woman. As women approach middle-age, a woman can be in a stage of menopause. In some embodiments, the subject can be a premenopausal woman. In other embodiments, the subject can be a perimenopausal woman. In still other embodiments, the subject can be a menopausal woman. In yet still other embodiments, the subject can be a postmenopausal woman. In other embodiments, the subject can be a man. The serum estradiol level of the subject can vary. In some embodiments, the serum estradiol level (E2) of the subject can be in the range of >15 pg/mL to 350 pg/mL. In other embodiments, the serum estradiol level (E2) of the subject can be ≤15 pg/mL. In other embodiments, the serum estradiol level (E2) of the subject can be ≤10 pg/mL.

Following breast cancer treatment, a subject can relapse or have reoccurrence of breast cancer. As used herein, the terms "relapse" and "reoccurrence" are used in their normal sense as understood by those skilled in the art. In some embodiments, the subject has relapsed after a previous treatment for breast cancer. For example, the subject has relapsed after receiving one or more treatments with a SERM, a SERD and/or aromatase inhibitor, such as those described herein.

Various types of breast cancer are known. In some embodiments, the breast cancer can be ER positive breast cancer. In some embodiments, the breast cancer can be ER positive, HER2-negative breast cancer. In some embodiments, the breast cancer can be local breast cancer (as used herein, "local" breast cancer means the cancer has not spread to other areas of the body). In other embodiments, the breast cancer can be metastatic breast cancer.

As described herein, Compound (A), or a pharmaceutically acceptable salt thereof, or a pharmaceutical composition as described elsewhere herein, can be administered to such subjects by a variety of methods. In any of the uses or methods described herein, administration can be by various routes known to those skilled in the art, including without limitation oral, intravenous, intramuscular, topical, subcutaneous, systemic, and/or intraperitoneal administration to a subject in need thereof.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 500 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of Compound (A), or pharmaceutically acceptable salts thereof, can be determined by comparing their in vitro activity, and in vivo activity in animal models. Such comparison can be done by comparison against an established drug, such as fulvestrant.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the estrogen receptor dependent and/or estrogen receptor mediated disease or condition to be treated and to the route of administration. The severity of the estrogen receptor dependent and/or estrogen receptor mediated disease or condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

The in vitro anti-proliferation effect of Compound (A) was evaluated in MCF-7 cells engineered to express an ESR1 mutant (Y537S) using CRISPR knock-in technology. The in vivo antitumor efficacy of Compound (A) was evaluated in ESR1 mutant (Y537S & L536P) tumors derived from breast cancer patients.

Cell Proliferation Assay

Cells were seeded at 3000 cells/well in 96 cell plates in hormone depleted medium. After overnight incubation, cells were treated with compounds at indicated concentrations in the presence of estradiol (0.1 nM) for 6 days. CellTiter-Glo luminescence cell viability assay (Promega) was used to measure inhibition of cell proliferation.

Patient Derived Xenograft Tumor Model

Figure 3:
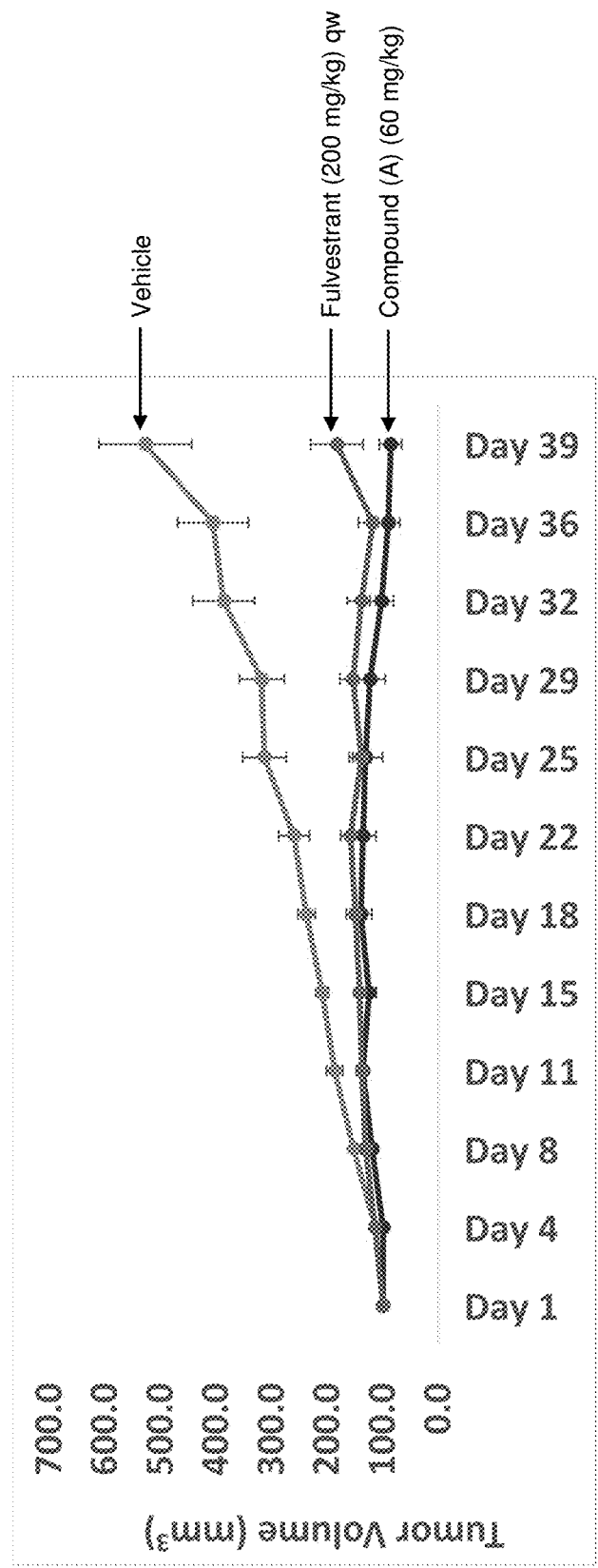
FIG. 3 shows the results of a tumor study with several compounds, including Compound (A), in a breast cancer model that has a L536P mutation.
Figure 4:
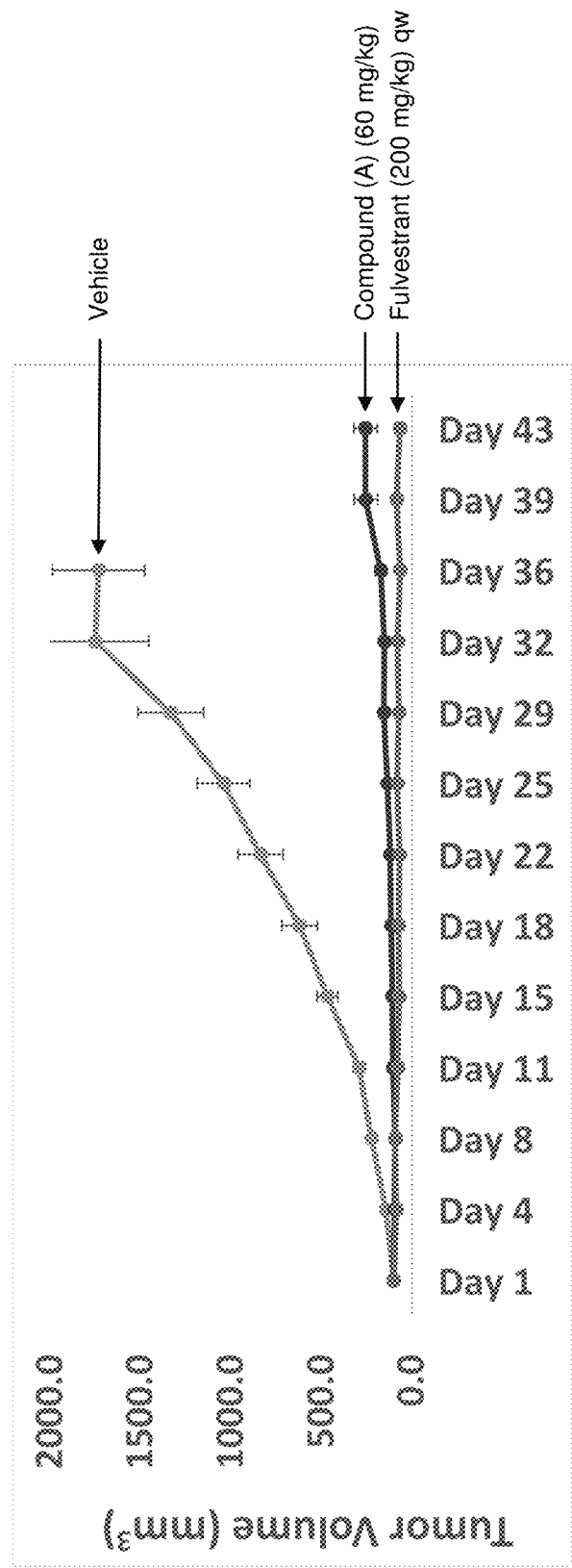
FIGS. 4 and 5 show the results of a tumor study with several compounds, including Compound (A), in a breast cancer model that has a Y537S mutation.
Figure 5:
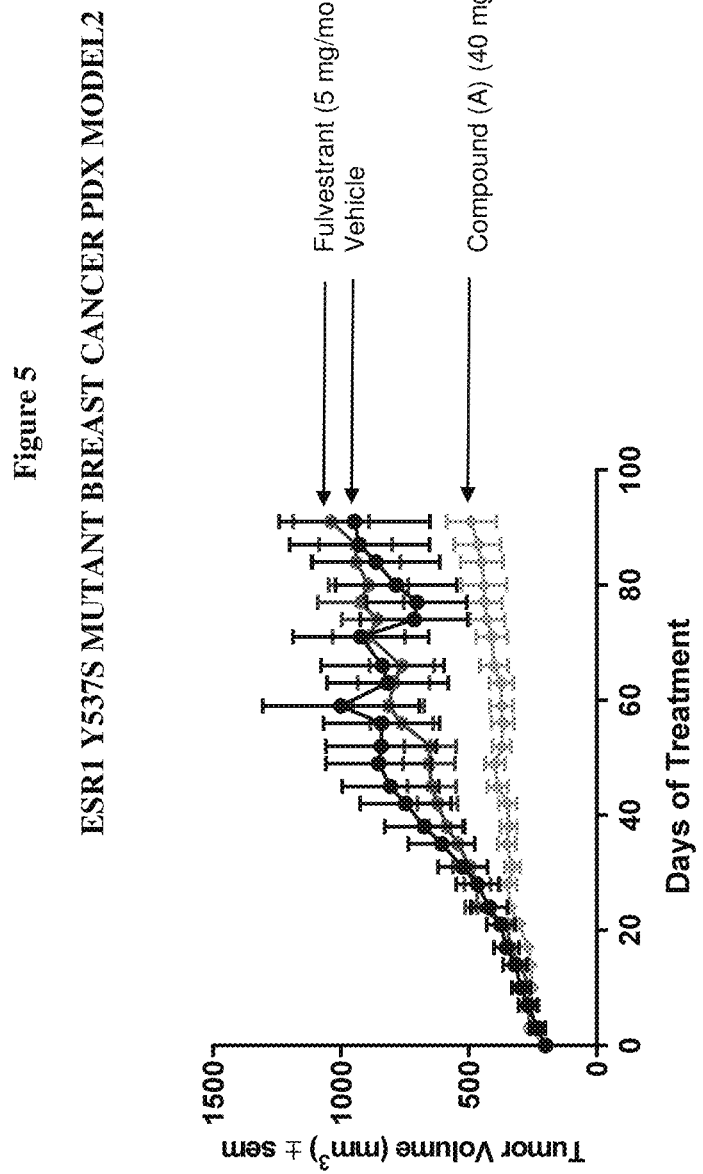

For the studies where the results are shown in FIGS. 3 and 4, tumor fragments for breast cancer patient derived xenograft (PDX) models were implanted into mammary fat pads of NSG mice. When tumors reached approximately 100 mm$^3$, mice were randomized into one of the following five treatment groups: vehicle control, Fulvestrant (200 mg/kg, subcutaneous injection, once per week), Compound (A) (60 mg/kg, oral dosing daily). For the study where the results are shown in FIG. 5, female athymic nude mice were implanted subcutaneously in the flank with 1.5×10$^6$ dissociated breast cancer patient derived xenograft (PDX) cells in 100 μl PBS:matrigel (1:1). When tumors reach 150-350 mm$^3$ (mean ~200 mm$^3$), animals were randomly distributed into treatment groups of 10 animals each and dosed with vehicle, fulvestrant 5 mg/mouse by subcutaneous injection once per week, Compound (A) 40 mg/kg oral daily. Tumor volumes were evaluated twice per week to calculate tumor volume over time, and mice were weighed twice per week as a surrogate for signs of toxicity.

The data in FIG. 2 demonstrates that Compound (A) effectively inhibits E2 induced cell proliferation in both ESR1 wild-type and mutant cells. Treatment of the ESR1 mutant tumors with Compound (A) induced robust antitumor activity as shown in FIGS. 3, 4 and 5. The data provided in both FIGS. 3 and 4 demonstrates that Compound (A) has antitumor activity against cancer cells that include a mutation within ESR1 that encodes ERα. Additionally, Compound (A) has demonstrated potency that is equal to or greater than Fulvestrant as shown in FIG. 3-5 when Compound (A) is dosed at a lower level compared to Fulvestrant.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for treating breast cancer in a subject having breast cancer comprising administering to the subject having breast cancer an effective amount of a compound, or a pharmaceutically acceptable salt thereof, wherein the compound is Compound (A), or a pharmaceutically acceptable salt thereof, having the structure:

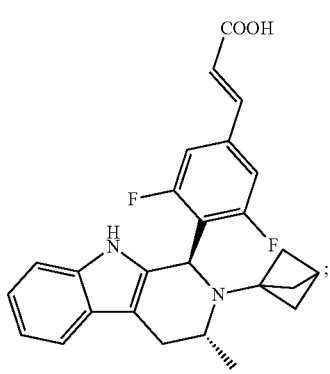

(A)

and
wherein the breast cancer has at least one point mutation within the Estrogen Receptor 1 (ESR1) that encodes Estrogen receptor alpha (ERα), wherein the mutation is selected from the group consisting of: Y537S and L536P.

2. The method of claim 1, wherein the breast cancer is ER positive breast cancer.

3. The method of claim 1, wherein the breast cancer is ER positive/HER2-negative breast cancer.

4. The method of claim 1, wherein the breast cancer is selected from the group consisting of local breast cancer, metastatic breast cancer and recurrent breast cancer.

5. The method of claim 1, wherein the subject has been previously treated with an endocrine therapy.

6. The method of claim 5, wherein the treatment was with a selective ER modulator (SERM).

7. The method of claim 6, wherein the selective ER modulator is selected from the group consisting of tamoxifen, raloxifene, ospemifene, bazedoxifene, toremifene and lasofoxifene.

8. The method of claim 5, wherein the treatment was with a selective ER degrader (SERD).

9. The method of claim 8, wherein the selective ER degrader is selected from the group consisting of fulvestrant, elacestrant, (E)-3-[3,5-Difluoro-4-[(1R,3R)-2-(2-fluoro-2-methylpropyl)-3-methyl-1,3,4,9-tetrahydropyrido[3,4-b]indol-1-yl]phenyl]prop-2-enoic acid, (R)-6-(2-(ethyl(4-(2-(ethylamino)ethyl)benzyl)amino)-4-methoxyphenyl)-5,6,7,8-tetrahydronaphthalen-2-ol, (E)-3-(4-((E)-2-(2-chloro-4-fluorophenyl)-1-(1H-indazol-5-yl)but-1-en-1-yl)phenyl) acrylic acid, (E)-3-(4-((2-(2-(1,1-difluoroethyl)-4-fluorophenyl)-6-hydroxybenzo[b]thiophen-3-yl)oxy) phenyl)acrylic acid, (E)-3-(4-((2-(4-fluoro-2,6-dimethylbenzoyl)-6-hydroxybenzo[b]thiophen-3-yl)oxy) phenyl)acrylic acid, (S)-8-(2,4-dichlorophenyl)-9-(4-((1-(3-fluoropropyl)pyrrolidin-3-yl)oxy)phenyl)-6,7-dihydro-5H-benzo[7]annulene-3-carboxylic acid and 3-(1R,3R)-1-(2,6-difluoro-4-((1-(3-fluoropropyl)azetidin-3-yl)amino) phenyl)-3-methyl-1,3,4,9-tetrahydro-2H-pyrido[3,4-b]indol-2-yl)-2,2-difluoropropan-1-ol.

10. The method of claim 5, wherein the treatment was with an aromatase inhibitor.

11. The method of claim 10, wherein the aromatase inhibitor is a steroidal aromatase inhibitor.

12. The method of claim 10, wherein the aromatase inhibitor is a non-steroidal aromatase inhibitor.

13. The method of claim 10, wherein the aromatase inhibitor is selected from the group consisting of exemestane, testolactone, anastazole and letrazole.

14. The method of claim 1, wherein the subject is a woman.

15. The method of claim 14, wherein the subject is a premenopausal woman.

16. The method of claim 14, wherein the subject is a perimenopausal woman.

17. The method of claim 14, wherein the subject is a menopausal woman.

18. The method of claim 14, wherein the subject is a postmenopausal woman.

19. The method of claim 1, wherein the subject is a man.

20. The method of claim 1, wherein the subject has a serum estradiol level in the range of >15 pg/mL to 350 pg/mL.

21. The method of claim 1, wherein the subject has a serum estradiol level ≤15 pg/mL.

22. The method of claim 1, wherein the mutation is Y537S.

* * * * *